United States Patent [19]

Lacey

[11] 4,262,368

[45] Apr. 21, 1981

[54] ROTATING AND HINGED KNEE PROSTHESIS

[75] Inventor: James A. Lacey, Winter Park, Fla.

[73] Assignee: Wright Manufacturing Company, Arlington, Tenn.

[21] Appl. No.: 78,451

[22] Filed: Sep. 24, 1979

[51] Int. Cl.³ ................................................ A61F 1/03
[52] U.S. Cl. .................................... 3/1.911; 128/92 C
[58] Field of Search ......................... 3/1.911; 128/92 C

[56] References Cited
U.S. PATENT DOCUMENTS 4,136,405  1/1979  Pastrick et al. ........................ 3/1.911

FOREIGN PATENT DOCUMENTS 1507309  4/1978  United Kingdom ..................... 3/1.911

Primary Examiner—Clifford D. Crowder
Attorney, Agent, or Firm—Scrivener, Clarke, Scrivener and Johnson

[57] ABSTRACT

A prosthesis for replacement of the human knee joint, having separate femoral and tibial components which after implantation are freely relatively rotatable about a proximal-distal axis and are hingedly connected about a transverse axis posterior of the axis of rotational movement.

2 Claims, 4 Drawing Figures

FIG. 1.
FIG. 3.
FIG. 4.
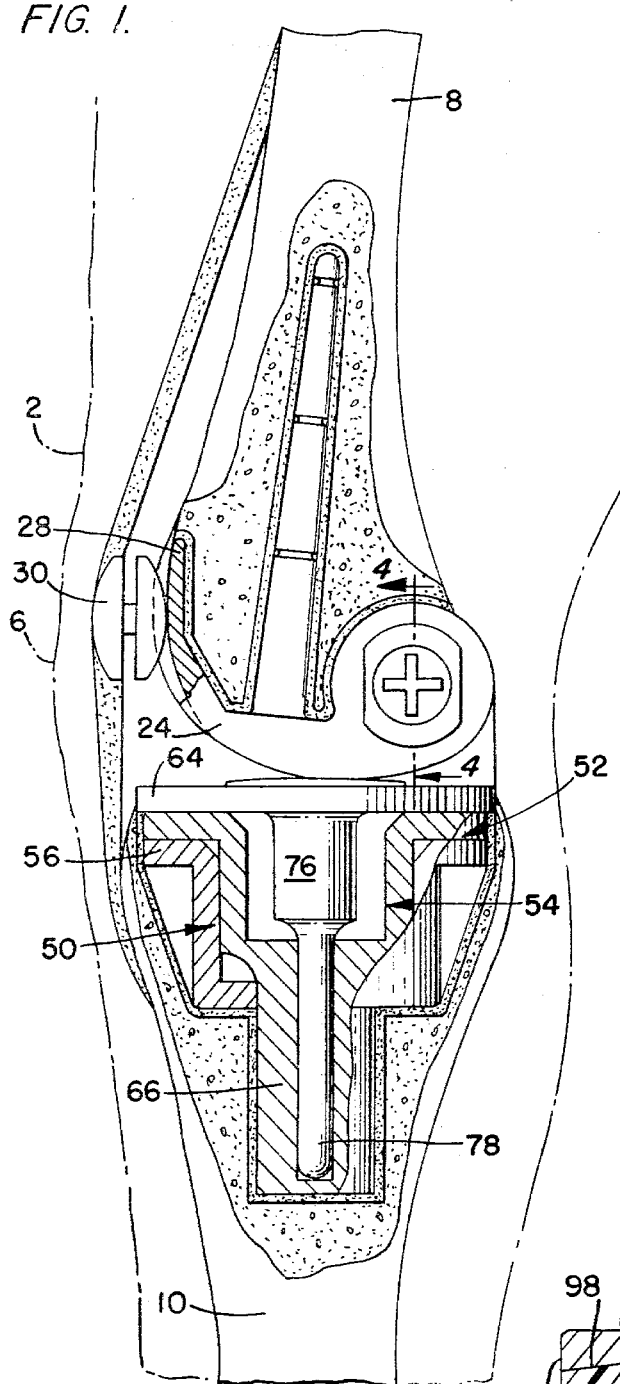
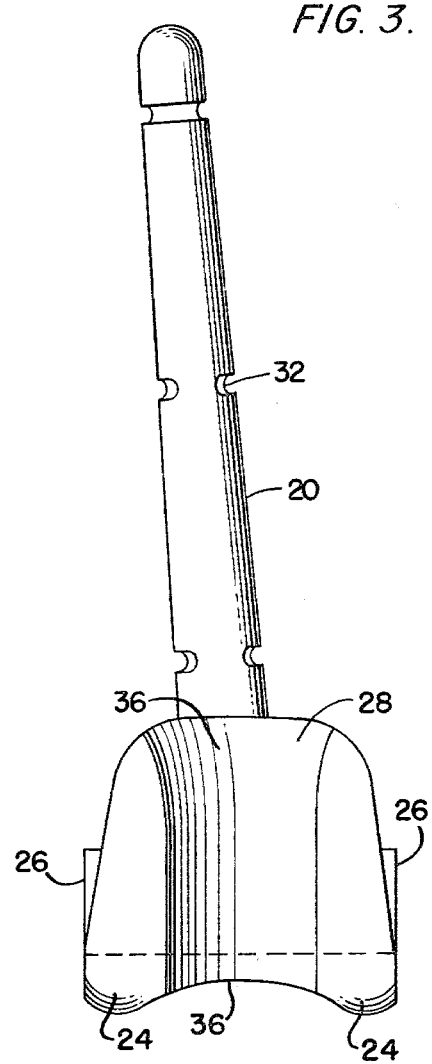
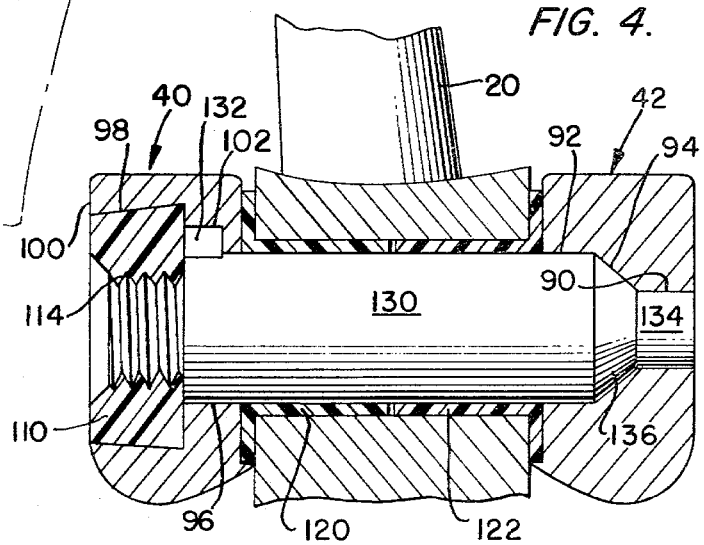

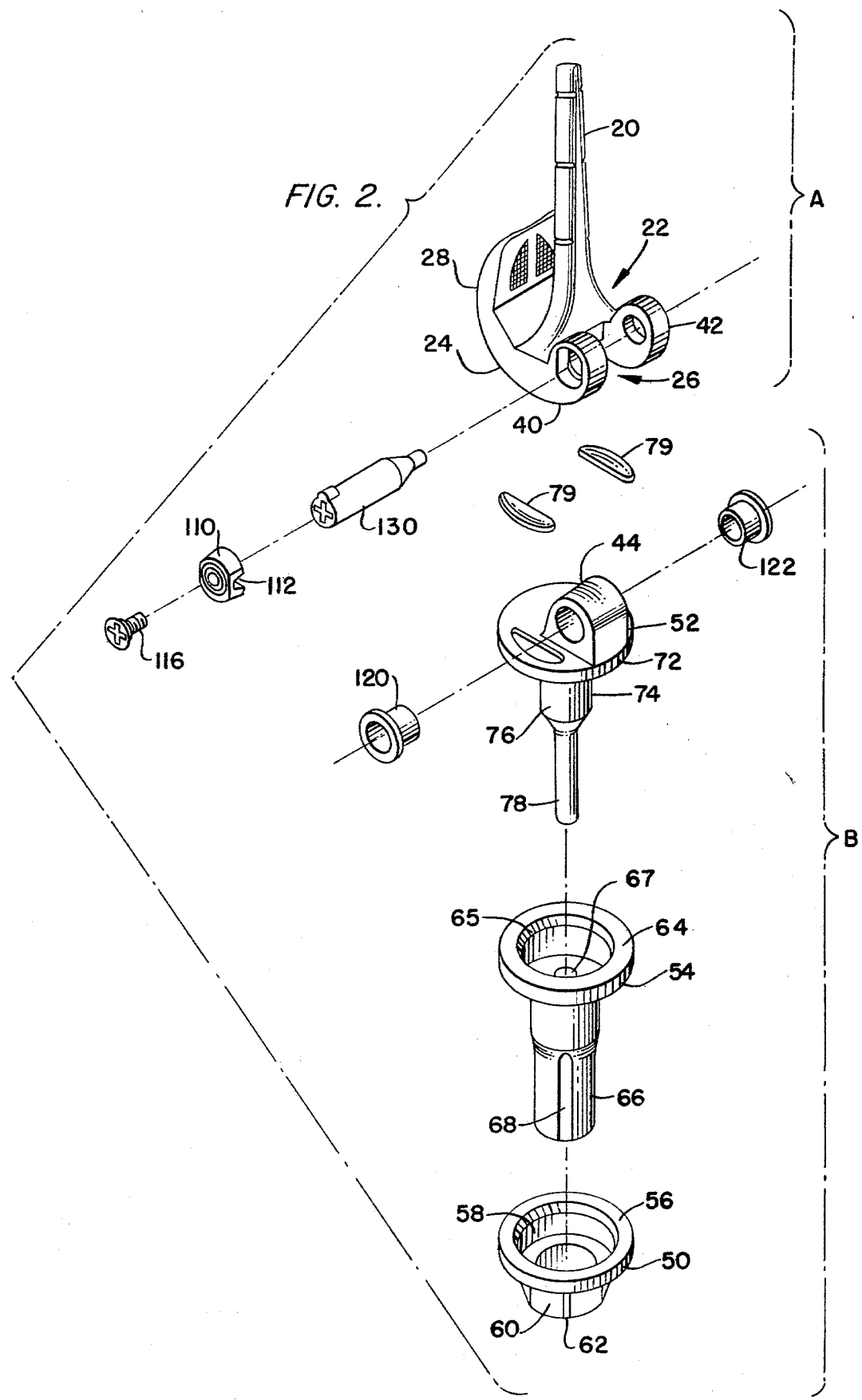

ROTATING AND HINGED KNEE PROSTHESIS

BACKGROUND OF THE INVENTION

The knee is generally regarded as being the most inherently unstable of the joints of the human body, due in part to the complex of inter-related types of motions to which the several knee elements are subjected during the normal acts of walking, running, climbing and the like, which include relative sliding and rolling movements as well as rotation about both horizontal and vertical axes. In the past various mechanical approaches have been proposed in the attempt to approximate, through an artifical joint, the natural action of the human knee. Advanced conditions of disease or serious traumatic injury of the knee joint complicate surgical repair and efforts to simulate the natural knee motion through use of a prosthesis.

Under circumstances wherein the condyles of the knee are beyond acceptable repair by means of surgical replacement of only the articular surfaces thereof, it has been common practice to attempt joint reconstruction by means of one or the other of three general types of prothesis, which are: a first type which relies on a mechanical hinge, a second which is characterized by a ball-and-socket arrangement, and a third in which the femoral and tibial components are unconnected. Each of these has typical advantages and disadvantages of implantation and of therapeutic value.

The general objects of the present invention are to provide a new and improved joint prosthesis, generally of the hinged type, for the replacement of a seriously impaired human knee, which combines the mechanical strength of a pintle hinge with rotational freedom, which situates the horizontal pivot in a natural location posteriorly offset from the location of tibial-femoral contact, which affords ease of alignment and assembly during its surgical installation, and which incorporates means for absorbing any shock of engagement between the femoral and tibial components.

SUMMARY OF THE INVENTION

The knee prosthesis provided by the invention consists of a femoral component and a metal tibial plate both of which incorporate hinge means for connection during implantation, the femoral component having laterally spaced metal condyle replacing parts with an intermediate groove for engagement with an implanted patella button for lateral patella subluxation prevention, and the metal tibial plate being hinged to the femoral component and having silicone or polyethylene bumpers for absorption of engagement by the femoral component during flexion. The femoral component is mounted for full rotational movement in an assembly implanted in the tibia consisting of an inner tubular ployethylene liner which is non-rotationally supported within an outer annular metal base. An improved hinge means connecting the two components is provided.

DESCRIPTION OF THE DRAWINGS

FIG. 1 is a proximal-distal sectional view taken from the medial aspect of a human right knee implanted with a prosthesis according to the invention;

FIG. 2 is an exploded perspective view of the prosthesis;

FIG. 3 is an anterior view of the femoral prosthesis of FIG. 1, and

FIG. 4 is a view of the distal end of the femoral component showing the improved hinge joint, taken on line 4—4 of FIG. 1.

DESCRIPTION OF THE INVENTION

FIG. 1 of the drawings of this specification illustrate in broken line outline the knee region of the human right leg with the anterior indicated at 2, the posterior at 4, the knee at 6, the femur at 8 and the tibia at 10. Within these parts there is disclosed in implanted location a knee prosthesis comprising, as particularly identified in FIG. 2, a femoral component A and a tibial component B. The femoral component comprises an elongated stem 20 and a base member 22, the latter having parts 24 which replace the resected condyles, hinge-forming parts 26 which cooperate in connecting the femoral and tibial components, and a plate member 28 which slidably engages an artificial patella prosthesis 30.

The stem 20 of the femoral component is constructed and adapted for intramedullary implantation in the femur and is of sufficient length to provide secure implantation. The stem is downwardly tapered proximally and is provided with spaced annular grooves 32 to insure firm interlocking engagement with the bone cement conventionally used in the axially drilled femur.

The transversely spaced condyle replacing surfaces 24 of the base member 22 are integrally formed with the stem at its distal end and each has a distal surface of increasing radius anterior to posterior, the loci of the radii of successive increments lying in a J-shaped curve, as is well known in the art. The distal surface of the base member 22 is also formed with a central concave groove 36 of arcuate transverse shape which lies between the condyle replacing surfaces 24 and provides a track for the patella button 30 which, during the implantation of the prosthesis, is connected posteriorly to the patella. The posterior surface of the surface 24 may be provided with laterally spaced knurled surfaces which provide improved locking engagement with the prepared femoral bone surface.

The hinge forming means 26 are located at the posterior part of the base member 22 and comprise two laterally spaced generally externally cylindrical hinge-forming members 40, 42 which have axially aligned openings which are constructed and adapted to co-operate with a hinge member 44 on the tibial component whereby the two components are connected for flexional movement.

The tibial component B comprises three principal elements which, when implanted, are a distal metal base member 50, a proximal metal plateau member 52, and an intermediate bushing 54 which is formed of polyethylene or an equivalent synthetic plastic material. The metal base element 50 is cup-shaped in configuration and proximally has an annular flange 56 which surrounds an internal cup-shaped recess 58 from which there extends distally a tubular body 60 having proximally-distally extending ridges 62 which after implantation prevent rotation of the base member in the prepared bone.

The intermediate bushing 54 comprises a proximally located flange 64 which is constructed and adapted to be snugly positioned within the cup-shaped recess 58 of base member 50 and which surrounds a cup-shaped recess 65 in the proximal end of the bushing member. An elongated tubular part 66, having a central opening 67 throughout its length, extends distally from the inner periphery of the flange 64 and has such an outer diameter that it is snugly received within the central opening in the metal base member 50. A plurality, preferably four, shallow recesses 68 are formed in the outer surface of the tubular part 66 and extend longitudinally thereof and receive correspondingly shaped projections on the inner wall of the central opening in the metal base member to prevent relative rotational movement between the two parts.

The plateau member 52 comprises a circular flat metal plate 72 which is adapted to rest on the proximal surface of flange 64 of the bushing 54 and is provided with an elongated integrally formed part which extends distally from the lower surface of the plate in concentric relation thereto and comprises a proximal part 76 of circular cross sectional shape and of such dimentsions as to fit snugly within the cup-shaped recess 65 in the proximal end of busing 54, and a distally extending pin 78 of circular cross sectional shape which is constructed to be snugly received within the central opening 67 which extends proximally-distally through the bushing 54, thereby to permit free rotation between the plateau member 52 and the bushing 54. A hinge forming member 44 is integrally formed with the plate 72 and extends proximally from the upper surface thereof at the posterior part.

Means are provided for cushioning the impact of the condyle replacing surfaces of the femoral component on the proximal surface of the tibial plateau member 52 during flexing movement of the knee prosthesis, and such means comprise two bumpers 79 which are respectively positioned on the medial and lateral sides of the upper surface of the plateau member distal to the condyle replacing surfaces of the femoral component when the components are hingedly connected. These bumpers are formed of any non-metallic material which will absorb impact, and are preferably embedded in recesses formed in the plateau member with their proximal surfaces aligned and proximal to that surface.

The femoral and tibial components of the prosthesis are preferably interconnected during implantation, and improved hinge means are provided by the invention for making this connection. The hinge connection is primarily effected by inserting the tibial hinge forming member 44 between the femoral hinge forming members 40, 42 with the openings in the three parts aligned, and then permanently but releaseably connecting the hinge parts by means particularly provided by the invention, which are best illustrated in FIGS. 2 and 4. In accordance with this aspect of the invention femoral hinge part 42 is provided with an internal passage therethrough which is of circular cross section throughout and comprises an outer end part 90 of smaller diameter, an inner end part 92 of greater diameter and a connecting part 94 of frustoconical configuration. The other femoral hinge part 40 is provided with an internal passage therethrough of circular cross section throughout comprising and inner end part 96 of diameter equal to that of the inner part 92 of hinge part 42 and an end part 98 which is of frusto-conical shape with an end of greater diameter than part 96 where the two are adjacent and which decreases in diameter therefrom to the outer surface 100 of the hinge part 40. A generally semi-cylindrical locking recess 102 communicates with the inner end passage 96. A core 110 of frusto-conical shape, which is preferably formed of a synthetic plastic material such as polyethylene, is provided for filling the tapered recess 98 in the femoral hinge part 40 and is split as shown at 112 so that it may be compressed from its normal configuration as shown in FIG. 2 to the installed position shown in FIG. 4. This core has a threaded internal opening 114 therethrough to receive a screw 116, which, when installed, expands the core and locks it in place.

The hinge forming part 44 of the tibial component has a passage therethrough which is constructed and adapted to receive, from its two ends, two tubular bushings 120, 122 which are formed of a synthetic plastic material and which provide a continuous opening having internal diameter equal to the internal diameter of the parts 92, 96 of the femoral hinge forming parts 40, 42.

The femoral and tibial components are connected during implantation to permit flexion of the total prosthesis, and this is effected by a hinge pin 130. This pin extends from the outer end of femoral hinge forming member 42 to the outer end of the part 96 of the femoral hinge forming member 40 and its outer end therefore abuts the inner face of the installed core 110. At its outer end adjacent core 110 the pin is provided with an external radially extending lug 132 which has the same shape as recess 102 in femoral hinge forming member 40 and is received within the recess when the pin is installed to thereby lock the pin against rotation. Throughout its length the pin is shaped in cross section to correspond to the passages through the hinge forming parts 40, 42, 44 and therefore has the reduced end part 134 and the frusto-conical part 136 which are received respectively in the correspondingly shaped parts 90, 94 of the hinge forming part 42, and throughout the rest of its length is of constant circular cross sectional shape and size whereby it is received within the passage 92 of hinge forming member 42, the passages through the bushings 120, 122 and the passage 96 in hinge forming member 40.

It will be seen that because of the cooperating construction of the hinge forming passages and the pin the completion of the hinge connection may be easily and quickly performed during the implantation of the prosthesis merely by aligning the hinge forming members 40, 42, 44, inserting the pin with its lug 122 within the recess 102, and installing core 110 and its expansion screw 116.

I claim:
1. A total knee joint prosthesis comprising:
   (a) a femoral component having the following elements:
      i. a proximal stem for intramedullary implantation in the femur,
      ii. a base member integrally connected to the distal end of the stem and having condylar surfaces of increasing radius from ananterior to posterior terminating in an anterior proximally directed patella engaging surface, and
      iii. laterally spaced axially aligned hinge pin receiving members on the base member positioned posteriorly of the stem,
   (b) a tibial component having the following elements:
      i. a distally positioned metal base member comprising a proximally located annular cup-shaped part having an annular flange, with proximally-distally extending opening therethrough,
      ii. an intermediately positioned bushing member formed of a synthetic plastic material having a proximally located annular flange positioned within the cup-shaped part of the tibial base member and surrounding a cup-shaped recess, and a depending tubular part extending through the opening in the tibial base member and connected thereto by means preventing relative rotation between the two members and being adapted for intramedullary implantation in the tibia, iii. a proximally positioned circular metal plate member having a proximal flat surface positioned to be engaged by the condylar surfaces of the femoral component, and a pin extending distally therefrom having a proximal part constructed to be received within the cup-shaped recess in the bushing member and a cylindrical pin extending distally therefrom and constructed to be snugly received within the bushing member, iv. a hinge pin receiving member integrally formed on the posterior proximal surface of the plate and extending proximally therefrom and adapted to be positioned between the hinge pin receiving members of the femoral component, and (c) a hinge pin extending through the interrelated hinge pin receiving members to provide a pivotal connection between the femoral and tibial components posterior to the stem.

2. The knee prosthesis according to claim 1 in which the hinge connection is characterized by the following:

i. one of the hinge pin receiving members of the femoral component has a passage (a) therethrough of circular cross sectional shape having an outer part (b) of smaller diameter, an inner part (c) of greater diameter, and a connecting part (d) of frusto-conical shape, ii. the other hinge pin receiving member of the femoral component having a passage therethrough of circular cross sectional shape having an inner part (e) of the same diameter as the inner part (c) of the passage through the one hinge pin receiving member, and an outer part (f) of larger diameter than parts (c) and (e) throughout which diverges toward the outer surface of the hinge receiving member, and an expandable core formed of a synthetic plastic material positioned within part (f) and having a screw threaded passage therethrough, iii. the hinge pin receiving member of the tibial component having a passage therethrough of constant diameter, bushings positioned in the opposite ends of said passage and having aligned openings therein of the same diameter which is equal to that of parts (c) and (e) of the hinge receiving parts of the femoral component, and iv. a hinge pin adapted to extend through the passages in the hinge receiving members of the femoral and tibial components and shaped throughout its length to snugly fit the passages in said parts, the pin being of such length that it extends from the outer end of the outer part (b) of the one hinge pin receiving member to the end of passage (e) in the other hinge pin receiving member.

* * * * *